(12) United States Patent  
Gil et al.

(10) Patent No.: US 8,217,059 B2
(45) Date of Patent: Jul. 10, 2012

(54) COMPOSITIONS AND METHODS FOR TREATING SPASTICITY

(75) Inventors: Daniel W. Gil, Corona Del Mar, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/883,949

(22) Filed: Sep. 16, 2010

(65) Prior Publication Data

US 2011/0212995 A1    Sep. 1, 2011

Related U.S. Application Data

(60) Provisional application No. 61/243,063, filed on Sep. 16, 2009, provisional application No. 61/246,284, filed on Sep. 28, 2009.

(51) Int. Cl.
*A01N 43/40*   (2006.01)
*A01N 43/36*   (2006.01)

(52) U.S. Cl. .................... 514/336; 514/422

(58) Field of Classification Search .............. None
See application file for complete search history.

(56) References Cited

U.S. PATENT DOCUMENTS

2009/0036436 A1    2/2009   LeBlond et al.

FOREIGN PATENT DOCUMENTS

| WO | WO 2006/081273 | 8/2006 |
| WO | WO 2008/011478 | 1/2008 |
| WO | WO 2008011487 A2 * | 1/2008 |
| WO | WO 2008/109610 | 9/2008 |
| WO | WO-2009/012082 | 1/2009 |
| WO | WO 2009/100095 | 8/2009 |

OTHER PUBLICATIONS

Watanabe et al, "*Role of Oral Medications in Spasticity Management*", PM&R, vol. 1, No. 9, pp. 839-841 Sep. 1, 2009.
O. Kakinohana, *Neuroscience*, 1:141(3), at 1569-83 (Sep. 2006).

* cited by examiner

*Primary Examiner* — Sreeni Padmanabhan
*Assistant Examiner* — Svetlana M. Ivanova
(74) *Attorney, Agent, or Firm* — Joel B. German; Krishna G. Banerjee

(57) ABSTRACT

Disclosed are methods of treating spasticity by administering to a patient in need of such treatment a compound having the following formula:

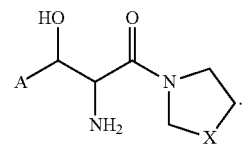

7 Claims, 1 Drawing Sheet

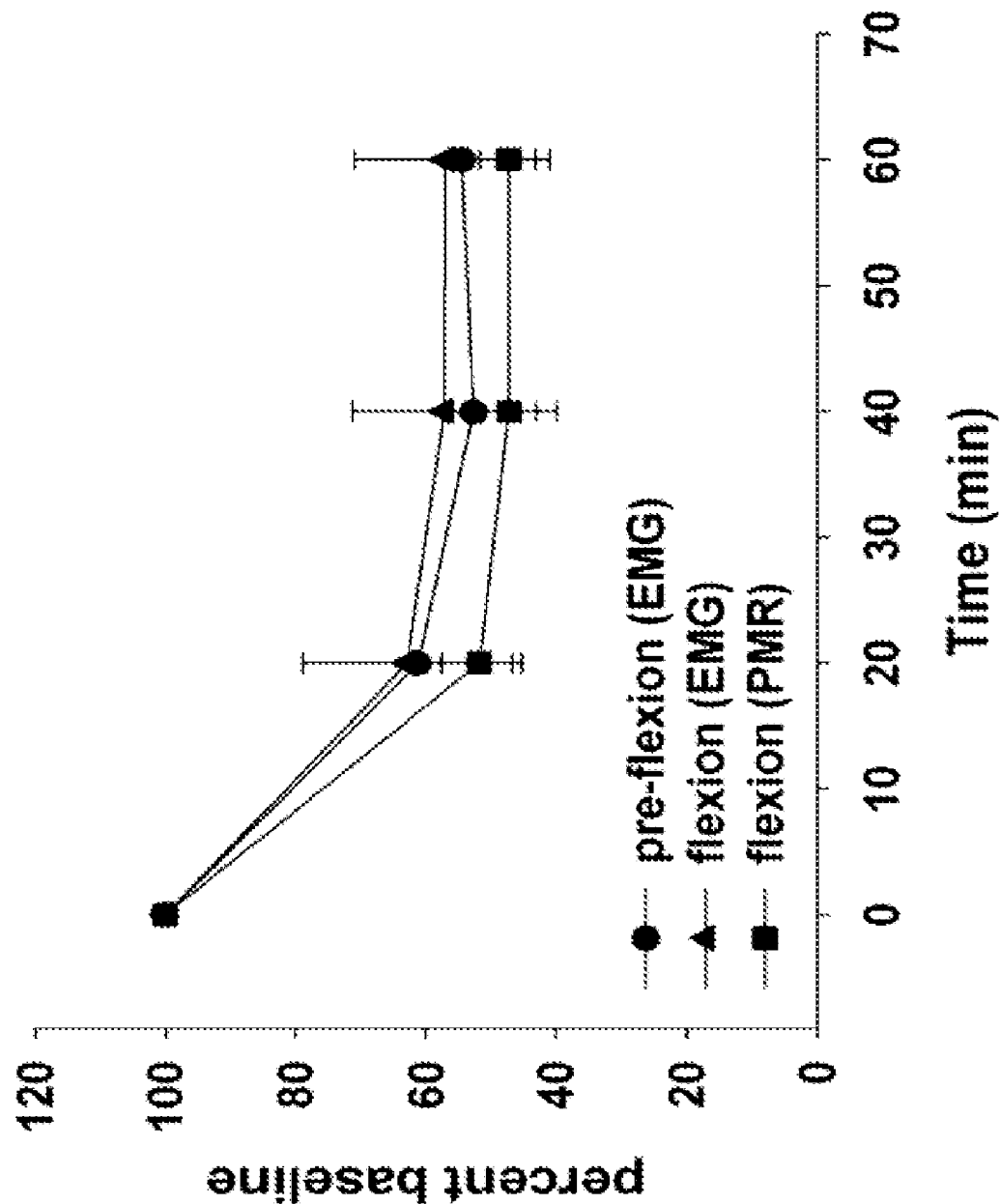

COMPOSITIONS AND METHODS FOR TREATING SPASTICITY

CROSS-REFERENCE

This application claims the benefit of U.S. Provisional Patent Application Ser. No. 61/243,063, filed on Sep. 16, 2009, and U.S. Provisional Patent Application Ser. No. 61/246,284, filed on Sep. 28, 2009, the entire disclosures of which are incorporated herein by this specific reference.

Disclosed herein is a method of treating spasticity by administering to a patient in need of such treatment a compound having the following Formula I:

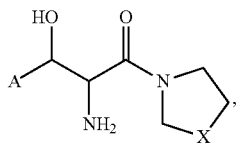

wherein X is $CH_2$ or $CH_2$—$CH_2$,
A is aryl, or is heteroaryl having 0, 1, 2, or 3 atoms selected from the group consisting of N, S, and O,
wherein A has 0, 1, 2, or 3 substituents each comprising 0 to 8 carbon atoms, 0 to 3 oxygen atoms, 0 to 3 halogen atoms, 0 to 2 nitrogen atoms, 0 to 2 sulfur atoms, and 0 to 24 hydrogen atoms.

BRIEF DESCRIPTION OF THE DRAWINGS

FIG. 1 shows that 100 mg/kg i.p. Compound A inhibits EMG response in rats with spasticity. Animals were tested at time zero, subsequently injected with 100 mg/kg ip, and evaluated by EMG, electromyogram, PMR-peripheral muscle resistance.

DETAILED DESCRIPTION OF THE INVENTION

Spasticity

Spasticity is a condition characterized principally by continuous muscle contraction, usually resulting in stiff or rigid muscles. Other, common symptoms include exaggerated deep tendon reflexes (such as the knee-jerk or other reflexes); hypertonicity (increased muscle tone); clonus (a series of rapid muscle contractions), especially when a muscle is touched or moved; muscle spasms; scissoring (crossing of the legs as the tips of scissors would close); and carrying a shoulder, arm, wrist, or finger at an abnormal angle or in a bent position due to muscle tightness.

The degree of spasticity varies from mild muscle stiffness to severe and uncontrollable muscle spasms. Spasticity can be very painful and, depending on the affected muscles, can result in an uncoordinated gait, stiff or deformed posture, and shortening of the range of limb movement. It can cause permanent muscle shortening and problems around the joints against which the two spastic muscles are supposed to move (contracture). It can be a permanent feature or brought on by a variety of factors such as fatigue, heat, or infection.

Spasticity may occur in association with spinal cord injury; damage to the brain because of lack of oxygen, stroke, or head injury; amyotrophic lateral sclerosis (Lou Gehrig's disease); phenylketonuria; metabolic diseases such as adrenoleukodystrophy; cerebral palsy; Stiff-man Syndrome; and multiple sclerosis (MS). In MS, it often affects the legs, although it can affect almost any muscle pair in the body. In multiple sclerosis, spasticity is usually caused by damage to the nerves (neurons) that control muscles or those that collect sensory information back from them. Reflexive spasms which are generated by the spinal cord are not inhibited by the brain, as normal, and increased muscle tone results. The lesions responsible are usually in the cerebellum or the white matter tracts that connect it to the peripheral motor (efferent) and sensory (afferent) nerves.

Compounds of the Invention

The method of the invention comprises administering to a patient compounds of Formula I:

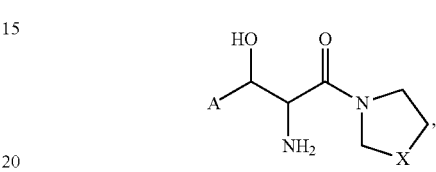

wherein X is $CH_2$ or $CH_2$—$CH_2$,
A is aryl, or is heteroaryl having 0, 1, 2, or 3 atoms selected from the group consisting of N, S, and O, and
wherein A has 0, 1, 2, or 3 substituents each comprising 0 to 8 carbon atoms, 0 to 3 oxygen atoms, 0 to 3 halogen atoms, 0 to 2 nitrogen atoms, 0 to 2 sulfur atoms, and 0 to 24 hydrogen atoms.

"Aryl," as used here, means any ring or ring system that contains at least one aromatic ring, such as phenyl, naphthyl, or biphenyl. Each ring may be substituted or unsubstituted.

"Heteroaryl," as used here, means an aromatic ring or aromatic ring system in which 1, 2, or 3 of the atoms in at least one ring are N, S, or O. This includes, for example, monocyclic aryl rings wherein at least one nitrogen, oxygen, or sulfur atom is in the ring, and bicyclic aromatic ring systems wherein at least one nitrogen, oxygen, or sulfur atom is in at least one of the rings. Examples of heteroaryl include pyridinyl, furyl, thienyl, benzothienyl, benzofuryl, quinolinyl, imidazolyl, thiazolyl, oxazolyl, and the like. Each ring may be substituted or unsubstituted.

The substituents may be the same or different. Examples of substituents having the constraints defined here include, but are not limited to, the following:

hydrocarbyl, meaning a moiety consisting of carbon and hydrogen only, including, but not limited to,
  a. alkyl, meaning hydrocarbyl having no double or triple bonds, including, but not limited to,
    i) linear alkyl, e.g. methyl, ethyl, n-propyl, n-butyl, n-pentyl, n-hexyl, etc.,
    ii) branched alkyl, e.g. iso-propyl, t-butyl and other branched butyl isomers, branched pentyl isomers, etc.,
    iii) cycloalkyl, e.g. cyclopropyl, cyclobutyl, cyclopentyl, cyclohexyl, etc., which may optionally be fused to another cycloalkyl or phenyl substituent;
    iv) combinations of linear, branched, and/or cycloalkyl;
  b. alkenyl, e.g. hydrocarbyl having 1 or more double bonds, including linear, branched, or cycloalkenyl;
  c. alkynyl, e.g. hydrocarbyl having 1 or more triple bonds, including linear or branched (alkynyl);
  d. combinations of alkyl, alkenyl, and/or alkenyl; alkyl-CN, such as —$CH_2$—CN, —$(CH_2)_2$—CN; —$(CH_2)_3$—CN, and the like;

hydroxyalkyl, i.e., alkyl-OH, such as hydroxymethyl, hydroxyethyl, and the like;

ether substituents, including —O-alkyl, alkyl-O-alkyl, and the like;

hydroxy alkyl ether, such as —COON, thioalkyl and thioether substituents, including —S-alkyl, alkyl-5-alkyl, and the like;

amine substituents, including —NH$_2$, —NH-alkyl, —N-alkyl$^1$alkyl$^2$ (i.e., alkyl$^1$ and alkyl$^2$ are the same or different, and both are attached to N), alkyl-NH$_2$, alkyl-NH-alkyl, alkyl-N-alkyl$^1$alkyl$^2$, and the like;

aminoalkyl, meaning alkyl-amine, such as aminomethyl (—CH$_2$-amine), aminoethyl, and the like;

ester substituents, including —CO$_2$-alkyl, —CO$_2$-phenyl, etc.;

other carbonyl substituents, including aldehydes; ketones, such as acyl

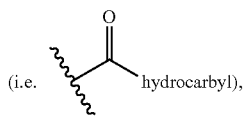

(i.e. hydrocarbyl), and the like; in particular, acetyl, propionyl, and benzoyl substituents are contemplated;

phenyl and substituted phenyl; the phenyl and substituted phenyl may itself be optionally fused with another phenyl or cycloalkyl substituent;

fluorocarbons and hydrofluorocarbons such as —CF$_3$, —CH$_2$CF$_3$, etc.;

—CN; and

—F, —Cl, —Br, or —I.

Combinations of the foregoing substituents are also possible, subject to the constraints defined.

Substituents must be sufficiently stable to be stored in a bottle at room temperature under a normal atmosphere for at least 12 hours, or stable enough to be useful for any purpose disclosed herein.

If a substituent is a salt, for example of a carboxylic acid or an amine, the counter-ion of said salt, i.e. the ion that is not covalently bonded to the remainder of the molecule is not counted for the purposes of the number of heavy atoms in a substituent. Thus, for example, the salt —CO$_2^-$Na$^+$ is a stable substituent consisting of 3 heavy atoms, i.e. sodium is not counted. In another example, the salt —NH(Me)$_2^+$Cl$^-$ is a stable substituent consisting of 3 heavy atoms, i.e. chlorine is not counted.

In one embodiment, A is pyridinyl, meaning that compounds of structures such as those shown below are contemplated. In these structures, R1, R2, and R3 are substituents as defined herein:

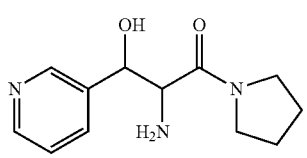

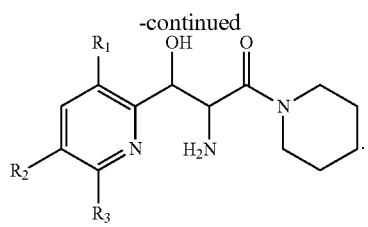

In another embodiment, A is thienyl, meaning that compounds of structures such as those shown below are contemplated. In these structures, R1 and R2 are substituents as defined herein:

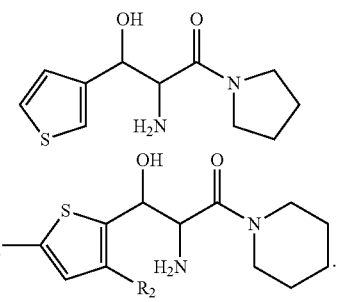

In another embodiment, A is furyl, meaning that compounds of structures such as those shown below are contemplated. In these structures, R1, R2, and R3 are substituents as defined herein:

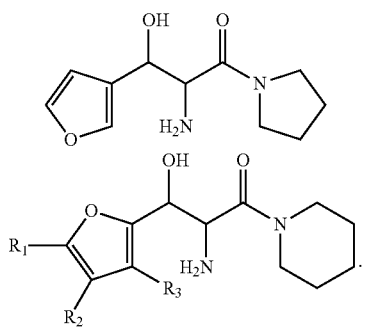

In one embodiment, each substituent is independently alkyl having from 1 to 8 carbon atoms.

In another embodiment, A is unsubstituted or has an isopropyl substituent.

In another embodiment, each substituent of A is —F, —Cl, —CH$_3$, or —CF$_3$.

In another embodiment, A is pyridyl, thienyl, furyl, pyrrolyl, pyrrolidinyl, imidazolyl, oxazolyl, thiazolyl, pyrazolyl, pyrimidinyl, quinolinyl, or pyrazinyl having 0, 1, 2, or 3 substituents.

Unless otherwise indicated, reference to a compound includes pharmaceutically acceptable salts, prodrugs, tautomers, alternate solid forms, and non-covalent complexes of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono, di and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Tautomers are isomers that are in rapid equilibrium with one another. They often, but do not necessarily, include a transfer of a proton, hydrogen atom, or hydride ion. For example, the structures herein are intended to include, but are not limited to, the tautomeric forms shown below:

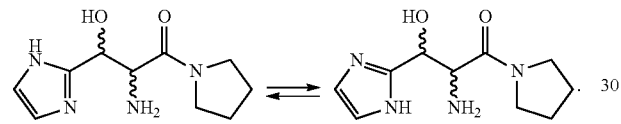

Unless stereochemistry is explicitly depicted, a structure includes every possible stereoisomer, both pure or in any possible mixture.

Alternate solid forms are different solid forms than ones that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Methods for producing the compounds of the invention are described in, for example, U.S. Patent Application Publication No. 2009/0036436, the disclosure of which is incorporated herein by reference.

Compositions useful in the method of the invention may further include an excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents.

Examples of compounds of the invention include the following

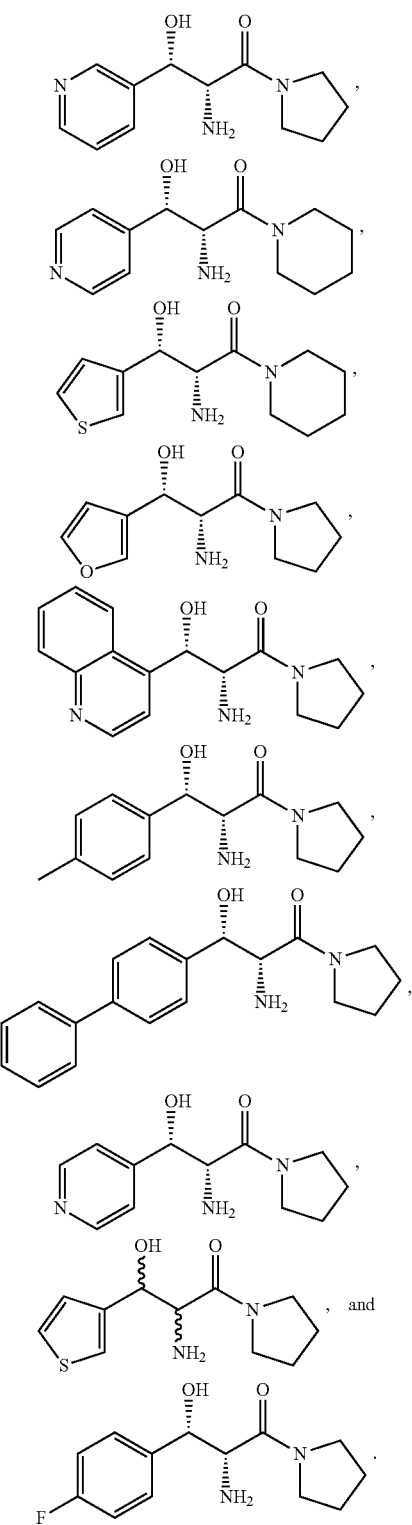

Methods of Treatment

The compounds described here may be used to treat a patient suffering from spasticity.

To "treat," as used here, means to deal with medically. It includes, for example, administering a compound of the invention to prevent the onset of spasticity, to alleviate its severity, and to prevent its reoccurrence.

The compounds of the invention may be administered at pharmaceutically effective amounts. Such amounts are normally the minimum dose necessary to achieve the desired therapeutic effect; in the treatment of spasticity, this amount would be roughly that necessary to reduce the frequency and/or severity of the symptoms to tolerable levels. For human adults, pharmaceutically effective amounts will generally be in the range of 1-1,000 mg/day, including 1-25 mg/day, 25-50 mg/day, 50-75 mg/day, 75-100 mg/day, 100-150 mg/day, 150-200 mg/day, 200-250 mg/day, 250-300 mg/day, 300-350 mg/day, 350-400 mg/day, 400-450 mg/day, 450-500 mg/day, 500-550 mg/day, 550-600 mg/day, 600-650 mg/day, 650-700 mg/day, 700-750 mg/day, 750-800 mg/day, 800-850 mg/day, 850-900 mg/day, 900-950 mg/day, 950-1,000 mg/day. Higher doses (1,000-3,000 mg/day) may also be effective. The actual amount of the compound to be administered in any given case will be determined by a physician taking into account the relevant circumstances, such as the severity of the spasticity, the age and weight of the patient, the patient's general physical condition, and the route of administration. In one embodiment, the compounds of the invention are administered at doses that are pharmaceutically effective but that do not cause sedation.

One means of evaluating the effectiveness of a dose is by evaluating muscle tone. In spasticity there is a disruption in the normal behavior of the stretch reflex that causes muscles, particularly the flexors, to be extremely resistive to passive stretch, that is, to be high in tone. As a result, motor control is severely impaired and stiffness or tightness of the muscles may interfere with gait, movement, and speech. Hence, assessing tone—the degree of resistance to stretch from an external source—is an important means by which one can evaluate the degree of spasticity that a patient has and the effectiveness of intervention.

One of the most widely accepted clinical measures of tone in spasticity is the Ashworth scale and the Modified Ashworth Scale. A clinician moves a patient's limbs about their joints and then assigns a grade to each limb corresponding to how much resistance the clinician feels. The Ashworth Scale is shown in Table 1, below:

TABLE 1

Ashworth scale

| Grade | Description |
|---|---|
| 1 | No increase in muscle tone |
| 2 | Slight increase in tone giving a catch when part is moved in flexion or extension |
| 3 | More marked increase in tone but only after part is easily flexed |
| 4 | Considerable increase in muscle tone |
| 5 | Passive movement difficult; affected parts are rigid in flexion or extension |

Other means to evaluate the effectiveness of a dose include biomechanical studies, such as those performed by a pendulum test; electrophysiologic studies, such as by electromyography (such as dynamic multichannel electromyography with gait studies) or Hoffman reflex studies (measuring deep tendon reflexes); and functional measurements, such as those given by the Barthel Index, Functional Independence Measure, and Fugl-Meyer Assessment of Sensorimotor Impairment (Fugl-Meyer scale), those functional measurement may be less accurate than the foregoing methods.

In one embodiment, the compounds of the invention are administered at doses that do not cause sedation. Current therapies for spasticity commonly produce sedation, in addition to a number of other undesirable side effects. Benzodiazepines (e.g. diazepam and clonazepam) are physically addictive drugs and can produce drowsiness and muscle weakness. Baclofen can produce muscle weakness, drowsiness, fatigue, and nausea, can interact dangerously with alcohol and other drugs, and can cause seizures and hallucinations if stopped suddenly. Dantrolene sodium can produce drowsiness, dizziness, weakness, fatigue, diarrhea, and skin photosensitivity, and in a minority of patients damages the liver. Tizanidine can produce drowsiness and occasionally low blood pressure, dry mouth, dizziness, and hallucinations, and damages the liver in a minority of patients. In one embodiment of the invention, in contrast, the compounds of the invention are administered at doses that are pharmaceutically effective yet do not cause sedation.

The patient may be given the compounds of the invention orally in any acceptable form, such as a tablet, liquid, capsule, powder, and the like. Other routes may be desirable or necessary, particularly if the patient suffers from nausea. Such other routes may include, for example, transdermal, intraperitoneal, parenteral, subcutaneous, intranasal, intrathecal, intramuscular, intravenous and intrarectal modes of delivery.

EXAMPLES

The inventors demonstrated the anti-spasticity effect of the compounds of the invention with Compound A, shown below:

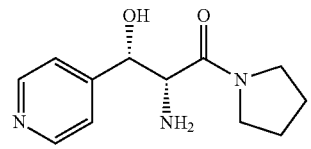

They show that Compound A inhibits the spasticity associated with transient ischemia of the spinal cord. The ischemic event induces a loss of GABAergic interneurons, which causes a subsequent increase in spinal motoneuron excitability. *Neuroscience,* 1:141(3), at 1569-83 (September 2006). Treatment of rats with 100 mg/kg of Compound A induces a decrease in muscle resistance during the period of ankle flexion and also corresponding changes in EMG activity. These data demonstrate that Compound A and other compounds of Formula I will be useful for treating spasticity. This could include spasticity associated with cerebral palsy, spinal cord injury, stroke, and multiple sclerosis.

Materials and Methods

Design and Experimental Groups

After ischemia, animals with developed paraplegia were selected and maintained for 3-12 months. To identify the presence of spasticity, the following tests were performed at 7-14 day intervals as described below: 1) tonic EMG activity recorded from gastrocnemius muscle (i.e., stimulus-independent changes in EMG activity); 2) peripheral muscle resistance measurement during a computer controlled ankle-flexion and simultaneous EMG recording from gastrocnemius muscle (i.e., stimulus-dependent changes in EMG activity); and 3) motor evoked potential recording.

Measurement of Peripheral Muscle Resistance

Peripheral muscle resistance was measured using a previously described system (O. Kakinohana, Neuroscience 1:141 (3) (2006)). Briefly, animals are placed into a plastic restrainer and one hind paw attached by a tape to a metal plate driven by a computer-controlled stepping motor. The metal plate is equipped with a digital force transducer. The resistance of the ankle to flexion was measured during motor-driven ankle flexion and data collected directly to the computer.

Electromyographic (EMG) Recordings During Ankle Flexion

To record EMGs, two silver needle (22 G) electrodes (distance between recording electrodes=1 cm) were placed percutaneously into the gastrocnemius muscle. Electrodes were connected to a preamplifier (HS4 fiber optic BIOAMP HEADSTAGE, WPI) and amplified using DB4 fiber optic amplifier (WPI). Animals were then allowed to acclimate for 10 min and the EMG responses recorded before, during and after ankle flexion. Recorded signal was digitized by the Instrunet Model 100 Network A/D, acquired by the Instrunet Model 200 PCI controller (Omega, USA) and stored in PC for analysis.

The results of this study are presented in FIG. 1, showing that 100 mg/kg i.p. Compound A inhibits EMG response in rats with spasticity. Animals were tested at time zero, subsequently injected with 100 mg/kg ip, and evaluated by EMG, electromyogram, PMR-peripheral muscle resistance.

What is claimed is:

1. A method for treating spasticity, the method comprising the step of administering to a patient in need of such treatment a compound having the following structure:

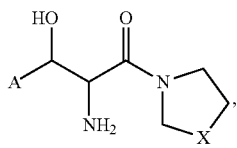

or a pharmaceutically acceptable salt thereof, wherein:
X is $CH_2$ or $CH_2$—$CH_2$,
A is aryl, or is heteroaryl having 1, 2, or 3 atoms selected from the group consisting of N, S, and O, and
wherein A has 0, 1, 2, or 3 substituents each comprising 0 to 8 carbon atoms, 0 to 3 oxygen atoms, 0 to 3 halogen atoms, 0 to 2 nitrogen atoms, 0 to 2 sulfur atoms, and 0 to 24 hydrogen atoms.

2. The method of claim 1, wherein A is selected from the group consisting of pyridinyl, thienyl, furyl, quinolinyl, methylphenyl, and biphenyl.

3. The method of claim 2, wherein A is unsubstituted.

4. The method of claim 2, wherein the spasticity is associated with spinal cord injury, stroke, head injury, amyotrophic lateral sclerosis, phenylketonuria, adrenoleukodystrophy, cerebral palsy, Stiff-man Syndrome, or multiple sclerosis (MS).

5. The method of claim 2, wherein the spasticity is accompanied by rigidity.

6. A method for treating spasticity to a patient in need thereof, the method comprising administering to said patient at least one compound selected from the group consisting of

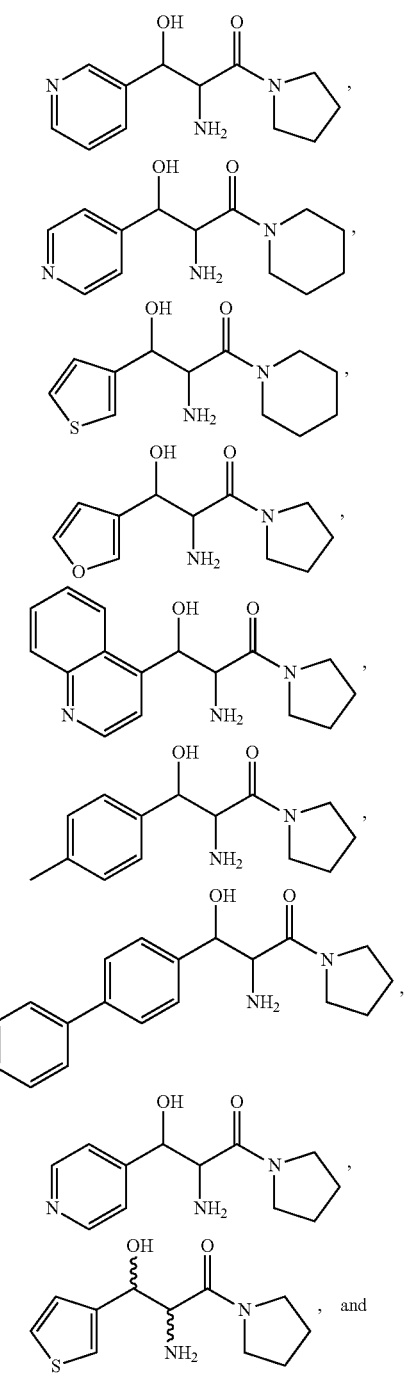

-continued
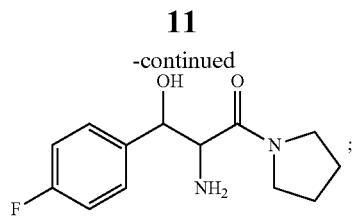
or a pharmaceutically acceptable salt thereof.
7. A method for treating spasticity in a patient in need thereof, the method comprising administering to said patient a compound of the formula
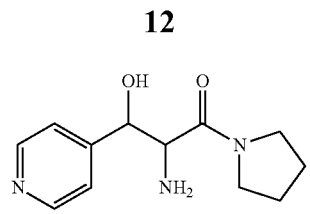
or a pharmaceutically acceptable salt thereof.
* * * * *